United States Patent [19]

Lattin

[11] Patent Number: 4,509,947
[45] Date of Patent: Apr. 9, 1985

[54] SELF-CLEANING DRUG DELIVERY CATHETER AND STORAGE BLADDER

[75] Inventor: Gary A. Lattin, Forest Lake, Minn.

[73] Assignee: Medtronic, Inc., Minneapolis, Minn.

[21] Appl. No.: 404,081

[22] Filed: Aug. 2, 1982

[51] Int. Cl.³ .............................................. A61M 25/00
[52] U.S. Cl. ..................................... 604/266; 604/20; 134/139; 310/800
[58] Field of Search ............ 128/24 A; 604/327, 266, 604/267, 20-23; 310/800; 134/1, 139 C

[56] References Cited

U.S. PATENT DOCUMENTS

| | | | |
|---|---|---|---|
| 2,989,725 | 6/1961 | Miller | 340/9 |
| 3,595,241 | 7/1971 | Sheridan | 604/267 |
| 3,680,544 | 8/1972 | Shinnick et al. | 128/2 R |
| 3,830,240 | 8/1974 | Antonevich et al. | 128/328 |
| 3,938,502 | 2/1976 | Bom | 128/2 V |
| 4,192,294 | 3/1980 | Vasilevsky et al. | 128/1 R |
| 4,283,461 | 8/1981 | Wooder et al. | 310/800 X |

Primary Examiner—Stephen C. Pellegrino
Attorney, Agent, or Firm—Reed A. Duthler; Joseph F. Breimayer; John L. Rooney

[57] ABSTRACT

A drug delivery catheter and storage bladder adapted for use in an implantable drug delivery system. The catheter and bladder are provided with piezoelectric layers adapted to be responsively coupled to a source of ultrasonic electrical signals. When so coupled, vibration of the piezoelectric layer dislodges any accumulation of crystallized drugs within the catheter and bladder.

1 Claim, 2 Drawing Figures

SELF-CLEANING DRUG DELIVERY CATHETER AND STORAGE BLADDER

CROSS REFERENCE TO COMMONLY ASSIGNED, COPENDING APPLICATION.

Reference is made to commonly assigned, copending U.S. Pat. application Ser. No. 406,197, by Dewitt J. Lowell for a "Robotic Implantable Medical Device and/or Component Restoration System" filed Aug. 9, 1982.

BACKGROUND OF THE INVENTION

1. Field of the Invention

This invention pertains generally to implantable medical devices, and more particularly, to implantable drug delivery systems.

2. State of the Prior Art

Various types of implantable drug delivery systems are well-known in the prior art. Most such systems employ a reservoir or storage bladder for containing the drug in fluid form, a delivery catheter leading from the storage bladder to a blood vessel, and means for controlling the flow of the drug into the blood vessel. Some systems rely on simple difusion of the drug into the blood vessel, however, most systems employ a pumping means to force the drug into the vessel.

Common to all systems is the need to fill the storage bladder at regular intervals. In order to provide for release of the drug over an extended period of time, these devices are often filled with a drug in concentrated solution. The high concentration of the drug, in some cases, can lead to crystalization and accumulation of the drug within the delivery catheter, the storage bladder, or the internal passageways of the drug delivery system. These accumulations may interfere with the flow of the drug through the delivery catheter and may interfere with accurate dosage determination if crystallization and accumulation occurs within the storage bladder.

SUMMARY OF THE INVENTION

The present invention is adapted for use in an implantable drug delivery system and is believed to avoid the above cited disadvantage of the prior art. By incorporating means for ultrasonically cleaning the interior of the delivery catheter and storage bladder, accumulation of crystallized drug within the system can be minimized or eliminated. The present invention is applicable generally to fluid chambers within the system which come in contact with the concentrated drug, and is not felt to be limited to the delivery catheter and storage bladder which are discussed in detail.

The present invention utilizes a layer of piezoelectric plastic adapted for connection to a source of ultrasonic electrical signals. Such piezoelectric plastics are known to the art, and have been used for applications including acoustic transducers (U.S. Pat. No. 4,322,877) and pressure wave sensors (U.S. Pat. No. 3,798,474). One such material, polyvinylidine fluoride ($PVF_2$) is commercially available from the Penwalt Corporation of King of Prussia, Pennsylvania. The material is prouduced in thin films having metallized layers of aluminum on their top and bottom surfaces. These films are capable of physical oscillation at frequencies up to 1 Megahertz (MHz).

In one embodiment of the invention, the delivery catheter or storage bladder is formed of an inner layer of an electrically insulative, fluid resistant plastic such as polyurethane, silicone rubber, or Teflon ®. Wrapped around or encasing the inner layer is a piezoelectric material, which may be $PVF_2$, with top and bottom surfaces metallized. Covering the metallized $PVF_2$ may be an outer layer of an insulative material such as polyurethane, silicone rubber, or Teflon ®. The metallized layers serve as electrodes for applying electrical signals across the piezoelectric layer. The inner and outer insulative layers serve to isolate the metallized layers from contact with tissue or with the drug solution, preventing chemical reaction with the metallized layers. The metallized layers are to be coupled to a source of ultrasonic electrical signals within the drug delivery system. Vibration of the piezoelectric layer at ultrasonic frequencies acts to clean accumulations of crystallized drug from the interior surfaces of the bladder and catheter. Periodic use of this invention will prevent any blockage of the delivery catheter by crystallized drug and prevent any accumulation of crystallized drug within the storage bladder.

BRIEF DESCRIPTION OF THE DRAWINGS

Other objects and many of the attendant advantages of this invention will be readily appreciated as the same becomes better understood by reference to the following detailed description when considered in connection with the accompanying drawings.

DETAILED DESCRIPTION OF THE PREFERRED EMBODIMENT

Figure 1:
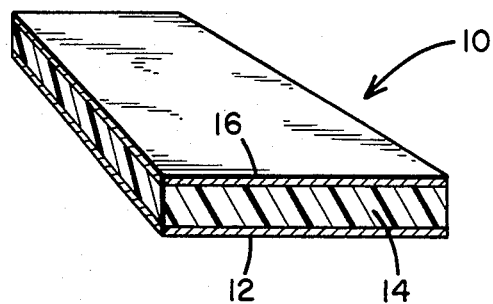
FIG. 1 is a cut-away perspective view of the piezoelectric layer and its associated metallic layers.

FIG. 1 illustrates the piezoelectric layer and its associated electrodes. The piezoelectric plastic 14, typically $PVF_2$, is provided with two metallized layers 12 and 16 which serve as electrodes. Metallized layers 12 and 16 are typically aluminum. Together, these components comprise an ultrasonic transducer 10.

Figure 2:
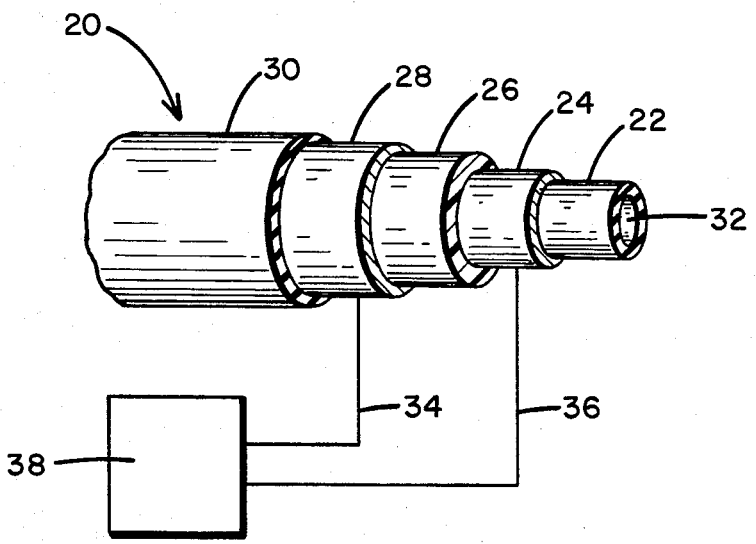
FIG. 2 is a fragmentary cut-away perspective view of a delivery catheter embodying the present invention.

FIG. 2 illustrates a drug delivery catheter according to the present invention. Catheter 20 is provided with an inner, tubular insulating layer 22 having a lumen 32 through which a drug may be delivered. Immediately external to insulating layer 22 is first metallized layer 24, which has been deposited on the inner surface of piezoelectric layer 26. Immediately surrounding and deposited on piezoelectric layer 26 is second metallized layer 28. Surrounding second metallized layer 28 is outer insulative layer 30. The connection of metallized layers 24 and 28 to ultrasonic electrical signal source 38 is diagrammed schematically. Suitable signal sources are known in the art.

Inner insulative layer 22 and outer insulative layer 30 may be fabricated of tubular silicone rubber, polyurethane, or other flexible, insulative moisture-resistant, biocompatible materials. Catheter 20 may then be formed by wrapping a strip of $PVF_2$ with associated metallized layers around inner insulative layer 22 and thereafter applying insulative layer 30. A drug storage bladder according to the present invention, may be manufactured in a similar fashion. Alternatively, catheter 20 may be produced by extruding a tube of $PVF_2$ to provide piezoelectric layer 26, thereafter applying metallized layers 24 and 28 using vacuum deposition, and finally applying insulative layers 22 and 30 if desired.

In use, metallized layers 24 and 28 are coupled to a source of ultrasonic electrical signals which cause piezoelectric layer 26 to vibrate. This vibration acts to clean the interior of the delivery catheter. A storage bladder incorporating the present invention functions in the same fashion.

Although the catheter shown in FIG. 2 employs layers of insulation over both metallized layers 24 and 28, catheters and bladders according to this invention do not require both insulative layers in all cases. By substituting a noble metal such as gold or platinum for aluminum, the metallized layers are made inert and do not require shielding from body tissue or from the drug solution. However, it is desirable that at least one layer of insulation be retained to prevent the formation of current leakage pathways between metallized layers 24 and 28 through the drug solution and body fluids. Further, although FIG. 2 shows a catheter having a piezoelectric layer completely encircling and covering the inner layer, a catheter having the piezoelectric material only at certain locations or having metallized layers only at certain locations is believed to be within the scope of the invention.

It must be understood that the various above-described embodiments have been given only by way of example, such other arrangements combining features shown in the accompanying drawings may be made without departing from the spirit and the scope of this invention. Consequently, such modified arrangements are properly, equitably, and intended to be within the full range of eqivalence of the following claims.

What we claim is:

1. A drug delivery catheter comprising a tubular catheter member having an interior surface; and piezoelectric means for cleaning the interior surface of said chamber by applying ultrasonic vibrations to said tubular catheter member; wherein said piezoelectric means comprises a layer of piezoelectric material applied to the tubular catheter member, a first metallized layer intermediate to said tubular catheter member and said layer of piezoelectric material and a second metallized layer external to said layer of piezoelectric material, and means whereby said piezoelectric material may be coupled to a source of ultrasonic electrical signals.

* * * * *